(12) United States Patent
Conzemius

(10) Patent No.: US 6,306,171 B1
(45) Date of Patent: Oct. 23, 2001

(54) TOTAL ELBOW ARTHROPLASTY SYSTEM

(75) Inventor: Michael G. Conzemius, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/543,160

(22) Filed: Apr. 4, 2000

Related U.S. Application Data

(63) Continuation-in-part of application No. 09/207,689, filed on Dec. 9, 1998, now Pat. No. 6,162,253.
(60) Provisional application No. 60/137,514, filed on Jun. 2, 1999.

(51) Int. Cl.⁷ .................................. A61F 2/58; A61F 2/30
(52) U.S. Cl. ...................................... 623/20.11; 623/18.11
(58) Field of Search ...................... 623/20, 20.11, 623/20.12, 20.13, 20.14, 20.22, 18.11

(56) References Cited

U.S. PATENT DOCUMENTS

| | | | |
|---|---|---|---|
| 3,656,186 | 4/1972 | Dee | 623/20.12 |
| 3,708,805 | 1/1973 | Scales et al. | 623/20.12 |
| 3,816,854 | 6/1974 | Schlein | 623/20.12 |
| 4,079,469 | 3/1978 | Wadsworth | 623/20.12 |
| 4,085,466 | 4/1978 | Goodfellow et al. | 3/1.91 |
| 4,206,517 | * 6/1980 | Pappas et al. | 623/20.13 |
| 4,219,893 | 9/1980 | Noiles | 3/1.911 |
| 4,224,695 | 9/1980 | Grundei et al. | 623/20.12 |
| 4,293,963 | * 10/1981 | Gold et al. | 623/20.11 |
| 4,364,389 | 12/1982 | Keller | 606/86 |
| 4,378,607 | 4/1983 | Wadsworth | 3/1.911 |

(List continued on next page.)

FOREIGN PATENT DOCUMENTS 0 493629 * 8/1992 (EP) ........................ 623/20

OTHER PUBLICATIONS

Olmstead, "The canine cemented modular total hip prosthesis," *Journal of the American Animal Hospital Association*, vol. 31, Mar./Apr. 1995, pp.109–124.

Sumner, et al., "Initial In Vitro Stability of the Tibial Component in a Canine Model of Cementless Total Knee Replacement," *Journal of Biomechanics*, vol. 27, No. 7, Jul. 1994, pp. 929–939.

Conzemius, et al., "Development and Evaluation of Semi-constrained Arthroplasty for the Treatment of Elbow Osteoarthritis in the Dog," Abstract in Veterinary and Comparative Orthopaedics and Traumatology, Apr. 1998, 11(4):A54.

Conzemius, et al., "Development and Evaluation of Semi-constrained Arthroplasty for the Treatment of Elbow Osteoarthritis in the Dog," Veterinary Orthopedic Society, 25th Annual Conference, Feb. 1998, p. 6.

(List continued on next page.)

*Primary Examiner*—Gene Mancene
*Assistant Examiner*—Michael B. Priddy
(74) *Attorney, Agent, or Firm*—Brobeck Phleger & Harrison, LLP

(57) ABSTRACT

A total elbow arthroplasty system, incorporating a humeral component, a radial component and a ball component, may be used as a total elbow replacement in the canine, as well as in other species. The implant of the present invention has an isometric humeral component and an isometric radial component. An isometric ball component having an isometric articular surface is mounted on the radial component. The humeral and radial components have stems for mounting in the medullary canals of the respective bones, which are angled so as to approximate the configuration of the original humerus and radius. The components work together to form a nonconstrained ball and socket joint. The invention is also directed to methods for implanting the novel endoprosthesis of the present invention in a canine elbow joint. The apparatus and methods of the present invention are useful in the treatment of elbow osteoarthritis in canines, as well as in other species, including other quadrupeds and humans.

20 Claims, 13 Drawing Sheets

U.S. PATENT DOCUMENTS

| | | | |
|---|---|---|---|
| 4,383,337 | 5/1983 | Volz et al. | 623/20.12 |
| 4,677,973 | 7/1987 | Slocum | 128/92 |
| 4,686,978 | 8/1987 | Wadsworth | 606/84 |
| 4,822,364 | 4/1989 | Inglis et al. | 623/20 |
| 4,834,081 | 5/1989 | Van Zile | 606/99 |
| 4,950,298 | 8/1990 | Gustilo et al. | 623/20 |
| 5,282,868 | 2/1994 | Bahler | 623/20 |
| 5,304,180 | 4/1994 | Slocum | 606/69 |
| 5,314,484 * | 5/1994 | Huene | 623/20 |
| 5,318,571 | 6/1994 | Benson | 606/102 |
| 5,330,533 | 7/1994 | Walker | 623/20 |
| 5,376,121 | 12/1994 | Huene et al. | 623/20 |
| 5,578,038 | 11/1996 | Slocum | 606/87 |
| 5,603,717 | 2/1997 | Benson | 606/102 |
| 5,683,468 | 11/1997 | Pappas | 623/20 |
| 5,782,923 | 7/1998 | Engelbrecht et al. | 623/20 |
| 5,788,705 | 8/1998 | Huddleston et al. | 606/102 |
| 5,800,558 | 9/1998 | LaHaise, Sr. | 623/23 |
| 5,879,389 | 3/1999 | Koshino | 623/20 |
| 5,879,395 | 3/1999 | Tornier et al. | 623/20 |
| 6,027,534 | 2/2000 | Wack et al. | 623/20 |
| 6,132,467 * | 10/2000 | Keller | 623/18.11 |
| 6,162,253 * | 12/2000 | Conzemius et al. | 623/20.11 |

OTHER PUBLICATIONS

Lewis, "Development of Elbow Arthroplasty (Canine) Clinical Trials," Sixth Annual ACVS Symposium Proceedings Small Animal, 1996, p. 110.

Kraay, et al., "Primary Semiconstrained Total Elbow Arthroplasty—Survival Analysis of 113 Consecutive Cases," *J Bone Joint Surg [Br]*, Jul. 1994, 76–B:636–40.

Morrey, et al., "Semiconstrained Total Elbow Replacement for Distal Humeral Nonunion," *J Bone Joint Surg [Br]*, Jan. 1995, 77–B:67–72.

Johnson, et al., "Incidence of Canine Appendicular Musculoskeletal Disorders in 16 Veterinary Teaching Hospitals from 1980 through 1989," *V.C.O.T.*, 1994, 7:56–69.

Huibregtse, et al., "The Effect of Treatment of Fragmented Coronoid Process on the Development of Osteoarthritis of the Elbow," *JAAHA*, Mar./Apr. 1994, 30:190–195.

Bouck, et al., "A comparison Surgical and Medical Treatment of Fragmented Coronoid Process and Osteochondritis Dissecans of the Canine Elbow," *V.C.O.T.*, 1995, 8:177–83.

Morrey et al., "Semiconstrained Arthroplasty for the Treatment of Rheumatoid Arthritis of the Elbow," *Journal of Bone and Joint Surgery*, Apr. 1992, 74A:479–490.

Conzemius, et al., "Effect of Total Elbow Arthroplasty in the Normal Dog," Veterinary Orthopedic Society, 26th Annual Conference, Feb. 27–Mar. 6, 1999, p. 33, and non–published paper representing materials presented at conference (28pp).

Conzemius, et al., "Effect of Total Elbow Arthroplasty in the Normal Dog," Abstract in *Veterinary and Comparative Orthopaedics and Traumatology*, Feb. 1999, 12(2):A5.

Lewis, G, "The elbow joint and its total arthroplasty. Part I. A state–of–the–art review," *Bio–Med Mater Eng*, 1996, 6:353–365.

Zafiropoulus et al., "An intramedullary aligned bone cutting jig for elbow replacement," *Med Eng Phys*, 1995, 17(2):111–114.

Photograph of multicomponent elbow endoprosthesis designed by Dr. Phil Vasseur et al. at the University of California at Davis, and believed to be in use on or before Dec. 1997.

Conzemius, M., "Total Elbow Arthroplasty in the Dog," Contemporary Issues in Canine Hip Replacement, San Diego, California Jun. 10–12, 1999 (3 pp).

* cited by examiner

TOTAL ELBOW ARTHROPLASTY SYSTEM

CROSS REFERENCE TO RELATED APPLICATIONS

This application claims the benefit of U.S. Provisional Patent Application Serial No. 60/137,514, filed Jun. 2, 1999 and entitled "Total Elbow Arthroplasty System" and is a continuation-in-part o US. patent application Ser. No. 09/207,689, filed Dec. 9, 1998 now U.S. Pat. No. 6,162,253 and entitled "Total Elbow Arthroplasty System."

BACKGROUND OF THE INVENTION

1. Field of the Invention

The present invention relates to a novel total elbow arthroplasty system. In particular, the present invention is directed to a total elbow implant incorporating a ball and socket joint, and methods for total elbow replacement. The apparatus and methods of the present invention are useful in the treatment of elbow osteoarthritis in canines, as well as in other species, including other quadrupeds and humans.

2. Description of the Background

Elbow osteoarthritis is the most common orthopedic problem of the front leg encountered by the small animal practitioner and veterinary surgeon. (Johnson J. A., et al., V.C.O.T. 7:56–69, 1994.) The etiology of elbow osteoarthritis (OA) is multifactorial, involving developmental conditions such as fragmentation of the medial coronoid process. osteochondrosis, asynchronous growth between the radius and ulna, ununited anconeal process, trauma and idiopathic causes. (Johnson J. A., et al., V.C.O.T. 7:56–69, 1994; Huibregtse B. A., et al., JAAHA 30:190–5, 1994.) The disease is frequently complicated by an early age of onset and patients that are bilaterally affected. (Huibregtse B. A., et al., JAAHA 30:190–5, 1994.) Medical (nonsteroidal anti-inflammatories and polysulfated glycosaminoglycans) and/or surgical management of these conditions frequently leads to unsatisfactory results. Huibregtse et al. provide evidence that less than 50% of dogs treated medically and less than 60% of those treated surgically for fragmentation of the medial coronoid process had long-term successful recoveries. (Huibregtse B. A., et al., JAAHA 30:190–5, 1994.) Bouck et al. provided more objective data using force plate gait analysis and documented that lameness did not significantly improve from pretreatment status following medical or surgical therapy. (Bouck G. R., et al., V.C.O.T. 8:177–83, 1995.)

Improvements in implant designs and surgical techniques have made total elbow arthroplasty a satisfactory treatment for arthritic disorders of the elbow in man. (Kraay M. J., et al., J Bone Joint Surg [Br] 76-b:636–40,1994.) ln two separate evaluations, 91% of total elbow arthroplasty cases had long-term excellent outcomes. (Morrey B. F., et al., J Bone Joint Surg [Br] 77-B:67–72, 1995.) (Morrey B. F., et al., J Bone Joint Surg [Am] 74-A:479–90, 1992.) Total elbow arthroplasty has been successfully used in man in cases of inflammatory arthritis, osteoarthritis, humeral nonunion and erosive arthritis. (Kraay M. J., et al., J Bone Joint Surg [Br] 76-b:636–40, 1994.) (Morrey B. F., et al., J Bone Joint Surg [Br] 77-B:67-72, 1995.) (Morrey B. F., et al., J Bone Joint Surg [Am] 74-A:479–90, 1992.)

Although a reliable canine total elbow replacement has not previously been commercially available, total joint arthroplasty has been used in the hind limb of dogs. Specifically, total hip arthroplasty for OA is used in dogs with much success; 95% of dogs have a satisfactory outcome following total hip replacement. (Olmstead M. L., JAAHA 31:109–24, 1995.) Canine total hip arthroplasty has been a multimillion dollar business in the U. S., Europe, and Japan for the last decade. Veterinarians and pet owners accept total joint replacement technology and the cost necessary to make it effective in the dog. The need for canine total elbow arthroplasty parallels that of canine total hip arthroplasty. In addition, many advances in human total knee arthroplasty are linked to successful research using canine models. (Sumner D. R., et al., J Biomechanics 27:929–39, 1994.)

Technology and designs available for human total elbow arthroplasty, although helpful, cannot be directly applied to dogs because of significant anatomical and economical differences. Dogs are quadrupeds and their forelimbs are weight bearing; current total elbow implants used in humans are not designed to withstand the cyclic loading that would occur if used in a dog. In addition, canine bones have more contour than human bones and have increased variability in size and shape.

Total elbow arthroplasty in the dog is not commercially available. There have been a number of unsuccessful attempts in the dog. A research group at the University of California at Davis led by Dr. Philip B. Vasseur devised a canine total elbow replacement system in 1995. The elbow replacement system was not studied in vivo before use in three client-owned dogs with naturally occurring elbow arthritis.

The system designed by Vasseur's group used multiple components: a humeral component, a radial component (composed of a radial tray and a radial insert), and an ulnar component. The ulnar and humeral components articulated in a nonconstrained fashion. The ulnar component loosely fit into the humeral component. The radial component articulated with both the humeral and ulnar components in an unconstrained manner. All three implants were designed and used for cemented fixation. All three components were non-isometric, or designed specifically for use in either the left or right limb.

Each of the three cases had an unsatisfactory result following total joint replacement because of implant failure. The research project was terminated (personal communication with Dr. Vasseur on October 1996. Malarticulation and loosening of the components led to decreased range of motion, inflammation and joint pain.

Another veterinary practitioner located in Lakeport, Calif., Ralph Lewis, has also designed and performed total elbow arthroplasty. The Lewis system is a constrained or hinged system which includes a humeral component, radial component, a wrist pin screw and a locking screw. In order to install the implant, an osteotomy of the lateral epicondyle of the humerus and the proximal ulna are necessary. These osteotomies require repair with bone plates after the implants are installed (Lewis, R. H., "Development of Total Elbow Arthroplasty (Canine) Clinical Trials," *Proceedings from the 6th Annual ACVS Symposium*, San Francisco, Calif, October 1996, p.110).

In addition to requiring removal of a substantial amount of bone and subsequent bone repair, this system is also undesirable because the components are fully constrained (i.e., hinged). When constrained systems are loaded, the majority of the stress is shifted to the implant-cement or implant-bone interface. Constrained systems typically loosen at these stressed interfaces and thus have a much shorter lifespan than unconstrained or semiconstrained systems. This leads to implant failure.

There is therefore a need for a canine total elbow replacement that provides a pain free joint which approximates normal range of motion.

SUMMARY OF THE INVENTION

The present invention overcomes the problems and disadvantages associated with current strategies and designs, and provides a total elbow replacement useful in the treatment of canine elbow arthritis.

The present invention incorporates the advantages of nonconstrained articulation and isometry of all components (no left or right). The present invention provides a nonconstrained, modular, total elbow, designed for implantation on the humerus and radius.

Accordingly, one embodiment of the invention is directed to an elbow endoprosthesis for use in a patient, such as a canine. The endoprosthesis comprises a humeral component, a radial component and a ball component. The ball component articulates with a socket in the humeral component and is designed or adapted to be mounted on the engagement portion of the radial component. The humeral component has a condylar or body portion and a stem portion. The condylar portion is adapted to be received in a resected portion of a distal humerus between the medial and lateral aspects of the humeral condyles of the patient. The condylar portion has an isometric articulating surface at its distal end comprising a concave surface or socket designed to match the profile of the ball component. The humeral stem portion is attached to the proximal end of the condylar portion and is adapted to be received in the medullary canal of the distal humeral shaft of the patient. The humeral stem portion preferably has a longitudinal axis which is angled cranially with respect to the condylar portion so that the condylar portion and stem portion approximate the original angle between the humeral condyle and the humeral shaft of the patient.

The radial component comprises a body portion, a stem portion that is blended into the body portion, and an engagement portion. The engagement portion is attached to the proximal face and preferably comprises a radial neck portion. The body portion has a proximal face and a distal face. The stem portion is attached to the distal face, and is adapted to be received in the medullary canal of the proximal radial shaft of the patient. The body portion of the radial component rests on the surface of the cut bone of the radius, but preferably does not rest on the ulna. The body portion is preferably blended into the neck portion that angles towards the center of rotation of the original elbow joint. The neck portion has a tapered flare (i.e., it is tapered so that the base is wider than the tip). This feature allows for a press fit fixation with the ball component.

The ball component is spherical and matches the inside dimensions of the articular surface of the humeral component. Specifically, the ball component comprises a spherical articular surface for articulation with the concave socket of the humeral component, thereby forming a ball and socket joint.

Another embodiment of the invention is directed to an elbow endoprosthesis for replacing an elbow comprising a ball and socket joint.

The present invention is also directed to methods of implanting the elbow endoprosthesis of the present invention. The system and methods disclosed herein have clinical usefulness in veterinary medicine for the treatment of elbow arthritis. They are also useful for designing a live animal model for the study of implantology in human medicine, such as bioactive cement, porous ingrowth, hormone stimulation of bone ingrowth and aseptic loosening.

One such method for implanting an elbow endoprosthesis in an elbow joint comprises the steps of removing the trochlea of the humerus, removing the articular surface of the radius (i.e., the radial head) and cancellous bone from the proximal medullary canal of the radius, and, in any order, implanting a humeral component into the medullary canal of the humerus, and implanting a radial component into the medullary canal of the radius. Optionally, the articular surface of the ulna may also be removed before implanting the radial component.

Preferably, the radial component is adapted to receive a ball component thereon and the humeral component has a concave socket articulating surface for articulating with the ball component. The ball component may be mounted on the radial component before or after the radial component is inserted into the medullary canal of the radius. Alternately, the ball component and radial component may be manufactured as a single integral piece.

Another embodiment of the invention is directed to a method of replacing a quadruped's elbow comprising removing the humeral trochlea and articular surface of the radius of the quadruped's elbow joint and affixing a ball and socket endoprosthetic joint in place of the removed tissue.

Other embodiments and advantages of the invention are set forth, in part, in the description which follows, and, in part, will be obvious from this description and may be learned from the practice of the invention.

DESCRIPTION OF THE INVENTION

As embodied and broadly described herein, the present invention is directed to novel apparatus and methods for total elbow arthroplasty. The apparatus and methods of the present invention are useful in the treatment of elbow osteoarthritis in canines, as well as in other species, including other quadrupeds and humans.

As will be understood by those skilled in the art, the following terms as used herein have the following meanings:

median plane—a plane which longitudinally divides the animal or object into equal right and left halves; the term may also be used to refer to dividing a limb along its axis.

cranial—toward or relatively closer to the head.

caudal—toward or relatively closer to the tail.

dorsal—toward or relatively closer to the back (top) of the head, neck, trunk, or tail.

ventral—toward or relatively closer to the underside of the head, neck, trunk, or tail.

medial—toward or relatively closer to the median plane.

lateral—away from or relatively further from the median plane.

proximal—when used in reference to the limbs it implies a position near or relatively closer to the trunk.

distal—when used in reference to the limbs it implies a position away from or relatively further from the trunk.

original—refers to the normal or physiologic state of the structure referenced. For example, the phrase "original angle" when used in reference to the angle between portions of the same bone, or between two different bones, refers to the normal, physiologic angle or angular relationship between the portions or bones referred to, in the particular individual or species referenced.

The total elbow implants of the present invention include a humeral component, a radial component and a ball component. The components used in the present invention allow for nonconstrained articulation in a ball and socket joint mode. This articulation between the components and the manner in which the components are implanted provide a number of advantages over prior designs.

Humeral Component

Figure 1:
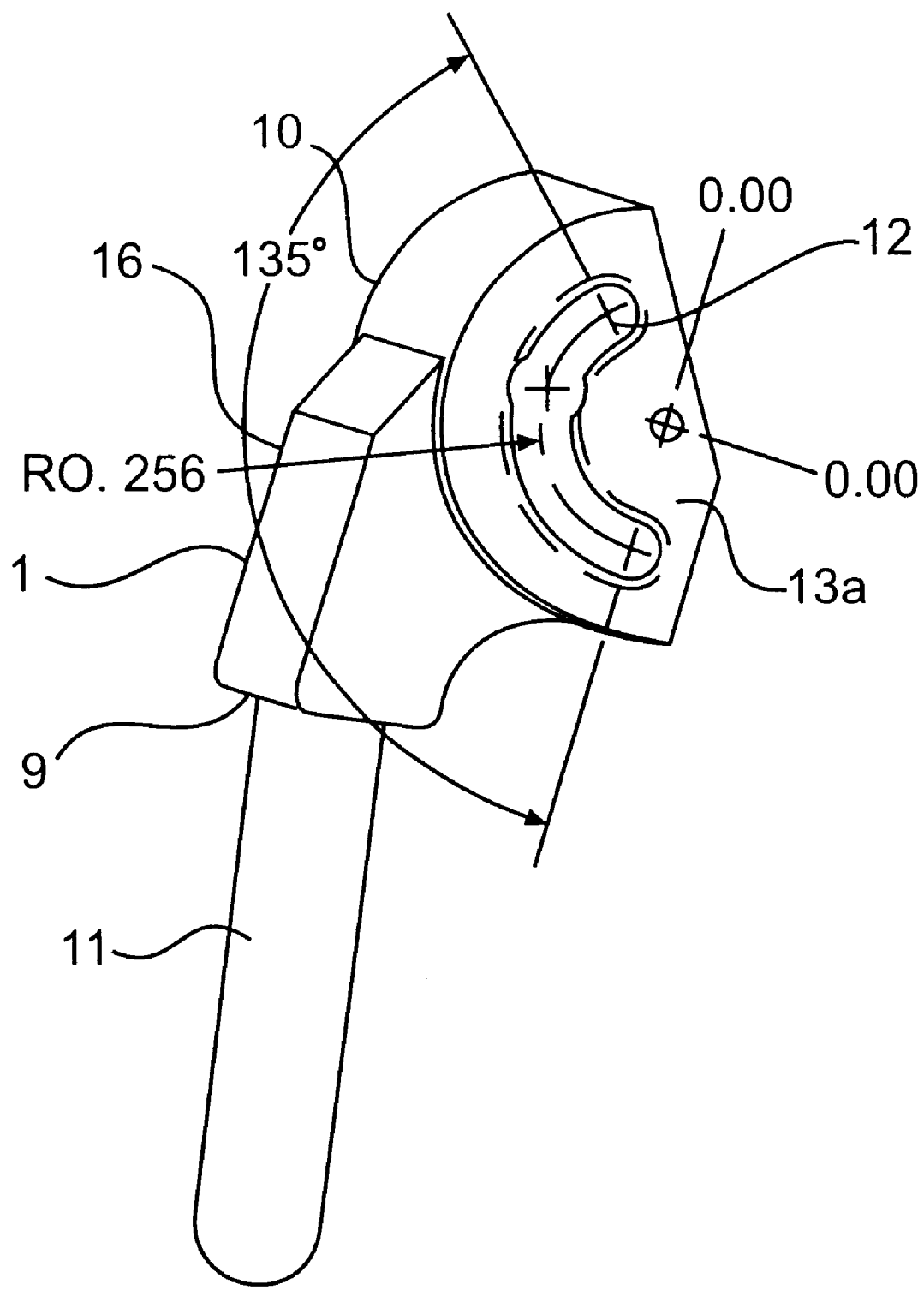
FIG. 1 is an oblique perspective view of a preferred embodiment of the humeral component of the present invention.
Figure 2:
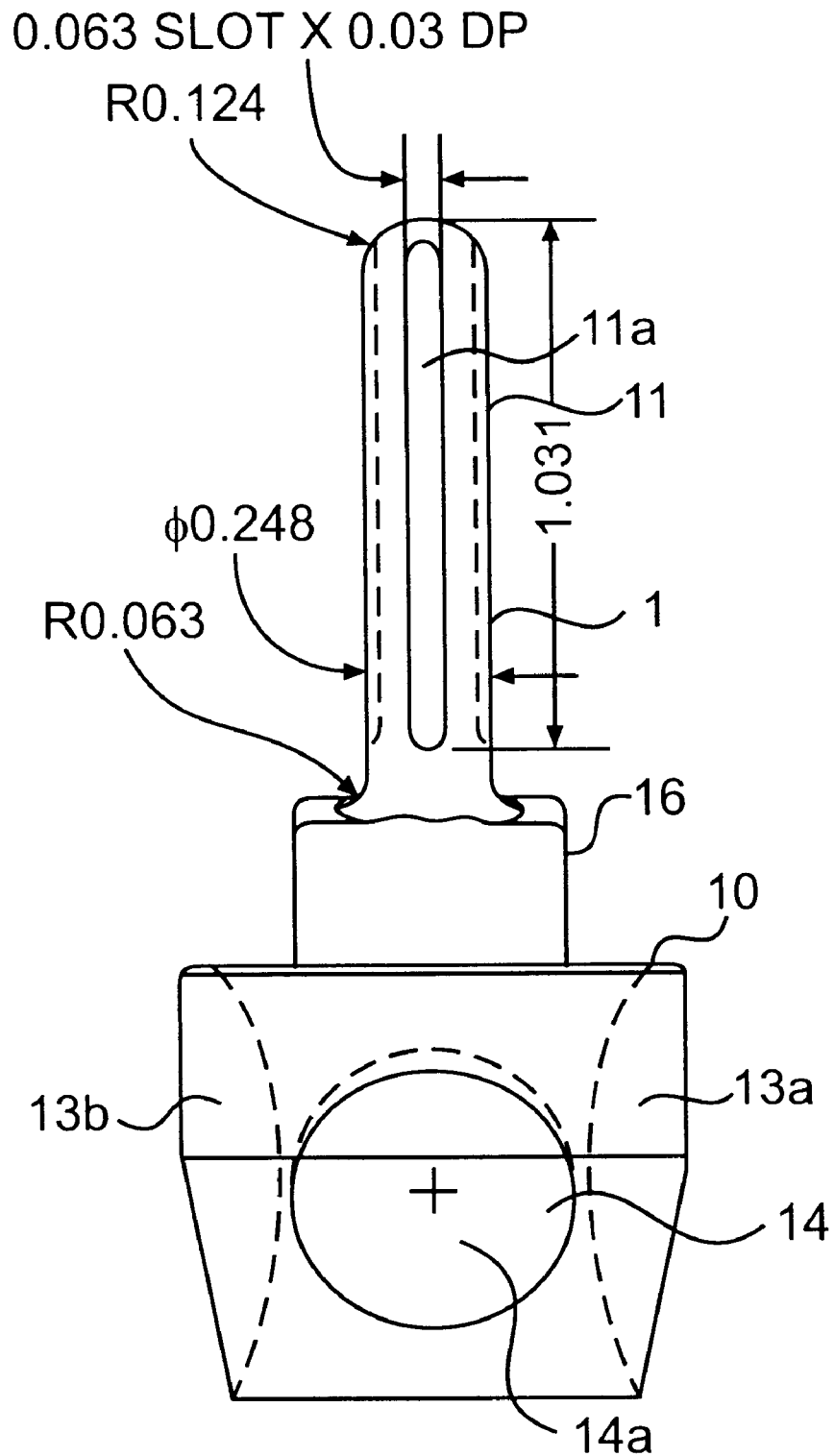
FIG. 2 is a front or cranial view of the humeral component depicted in FIG. 1
Figure 3:
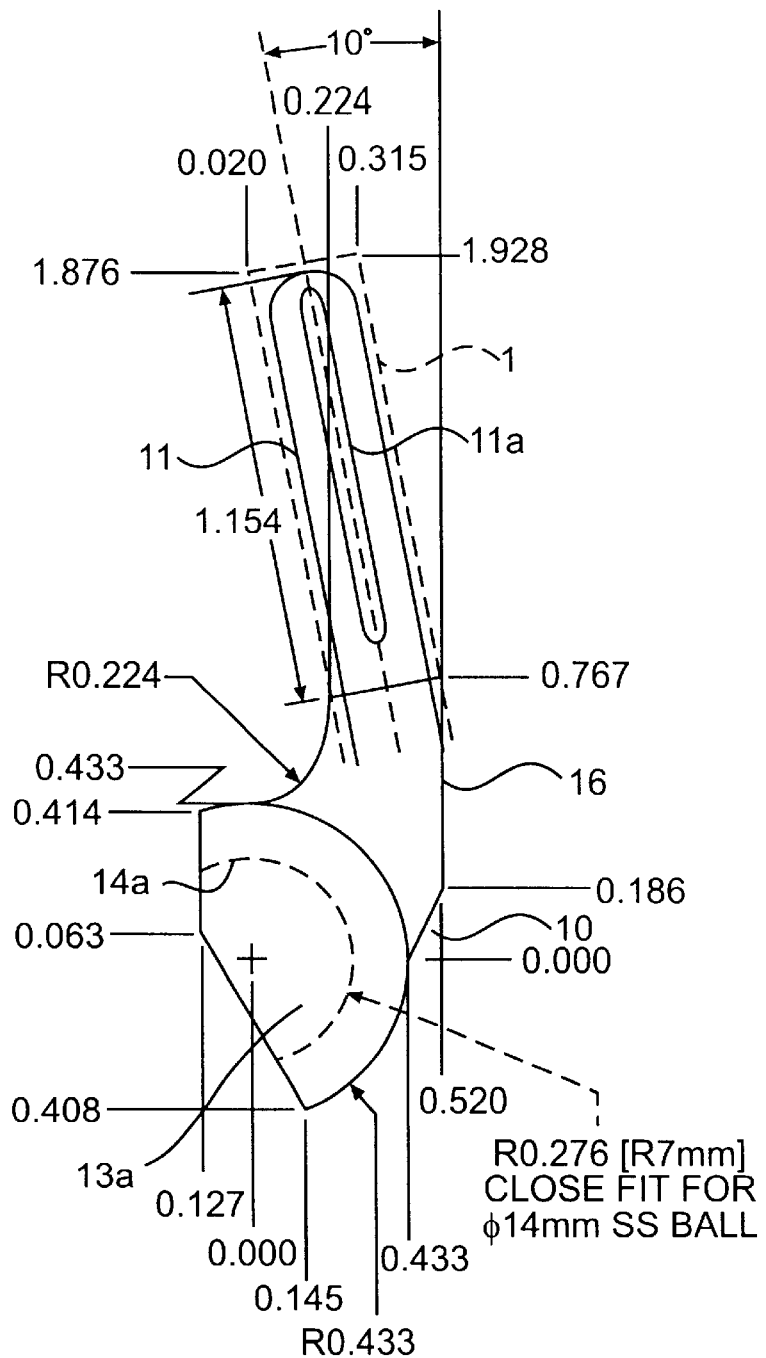
FIG. 3 is a lateral view of the humeral component depicted in FIG. 1.
Figure 4:
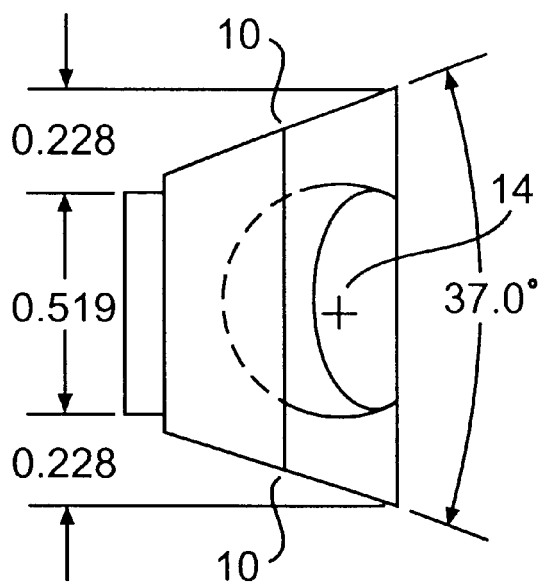
FIG. 4 is a bottom view of the humeral component depicted in FIG. 1.

FIGS. 1–4 depict the humeral component of a preferred embodiment of the elbow implant of the present invention. The humeral component, which provides the socket portion of the ball and socket joint described herein, is designed to be implanted in the humerus, as described below. In the figures, like reference numerals refer to like elements or features so that a further description thereof is omitted. FIG. 1 is an oblique perspective view of humeral component 1. FIG. 2 is a cranial view of humeral component 1. FIG. 3 is a lateral view of humeral component 1. FIG. 4 is a bottom view of humeral component 1.

Referring to FIGS. 1–4, humeral component I comprises a humeral stem portion 11 and a humeral body or condylar portion 10. Humeral condylar portion 10 comprises a proximal portion 16 at its proximal end, and an articulating surface 14 and two sides (flanges) 13a and 13b at its distal end. As detailed further below, stem portion 11 is preferably positioned with respect to condylar portion 10 such that it lies at an angle that matches the relationship between the original humeral condyles and the humeral shaft.

Concave articulating surface 14 is disposed on the craniodistal aspect of the distal end of condylar portion 10, midway between two sides (flanges) 13a and 13b. Articulating surface 14 is isometric and comprises a spherically concave surface 14a designed for engagement with ball component 3; it serves as the socket for a ball and socket joint. As can best be seen in FIG. 1, humeral component 1 of the preferred embodiment is entirely isometric, and can be used in either joint.

The longitudinal axis of humeral stem portion 11 is disposed so that it is angled cranially 0 to 20 degrees, more preferably, 5 to 10 degrees, and most preferably, 5 degrees with respect to the longitudinal axis of proximal portion 16 of condylar portion 10. Although the angle may be varied so long as it approximates the relationship between the original humeral condyles and the humeral shaft, in a preferred embodiment, the longitudinal axis of stem portion 11 is angled cranially approximately 5 degrees with respect to the longitudinal axis of proximal portion 16 of condylar portion 10, Thus, as can be seen in FIG. 3, the proximal end of stem portion 11 is more cranial than its distal attachment to proximal portion 16.

Figure 4A:
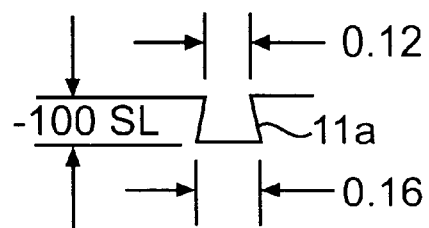
FIG. 4a shows a detail of a groove in the humeral component.

In a preferred embodiment, stem portion 11 is cylindrical in cross-section and is rounded at its most proximal end. Optionally, grooves 11a may be placed along the longitudinal axis of stem portion 11 to facilitate cementing of the component into position. Grooves 11a increase the cement-implant surface area, thereby reducing stress proportionally. Grooves 11a preferably have a reverse wedge or dovetail design, as depicted in FIG. 4a.

Proximal portion 16 of condylar portion 10 preferably has a greater cross-sectional area than stem portion 11, thereby forming a shoulder 9 at the junction where stem portion 11 is attached to proximal portion 16.

As can be best appreciated in FIGS. 3 and 4, sides 13a and 13b are preferably planar surfaces which are each angled towards the median plane of the implant, so that they are farther apart cranially than they are caudally, thereby matching the cut surfaces of the bone. Specifically, sides 13a and 13b may be angled 10 to 25 degrees, more preferably, 16 to 20 degrees, and most preferably, approximately 18½ degrees towards the median plane of the implant, so that they are farther apart cranially than they are caudally. Arcuate grooves 12 may be disposed in sides 13a and 13b and may have a reverse wedge or dovetail design to increase the cement-implant surface area and facilitate the interlocking of cement into the implant. Sides 13a and 13b are preferably round or arcuate around their caudal peripheries.

The outside dimensions of humeral component 1 are similar or preferably identical to the humeral component described in U.S. patent application Ser. No. 09/207,689 filed Dec. 9, 1998, incorporated herein by reference. The body or condylar portion 10 of the humeral component replaces abnormal bone and cartilage that has been removed from the patient's humeral condyle. The stem or stem portion is inserted into the medullary canal of the humerus. As in the humeral component described in U.S. patent application Ser. No. 09/207,689, the outside dimensions of the humeral component can be altered or modified for use in different sized patients and can be altered to be stabilized with either cement or porous ingrowth fixation.

In one preferred embodiment, a depression or groove may be provided in the caudal aspect of the distal end of condylar portion 10 of humeral component 1 to receive the anconeal process of the ulna. This feature allows the surgeon, if indicated, to preserve the bone of the ulna.

The curvature and profile of concave articulating surface 14 matches the curvature and profile of ball component 3, thereby allowing for smooth articulation. The radius of curvature of surface 14 may be modified depending upon the size of the implants, the thickness of component material (polyethylene, ceramic, metal) desired, or to simply match the radius of convex ball component 3 mounted on radial component 2. Humeral component 1 can be designed such that the body has variable sizes (small, medium, large), yet concave articular surface 14 remains the same. This allows for the system to be modular; the surgeon can pick and choose components based on patient size and ligament structure. All designs are compatible because the radius of curvature of the ball component is designed to match/articulate with the radius of curvature of the articular surface of all sizes of the humeral component.

Radial Component

Figure 5:
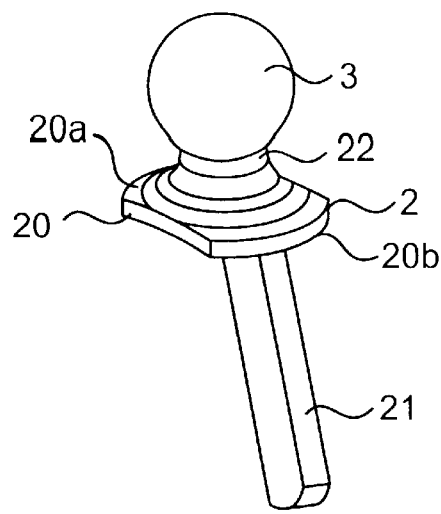
FIG. 5 is an oblique perspective view of a preferred embodiment of the radial component of the present invention.
Figure 6:
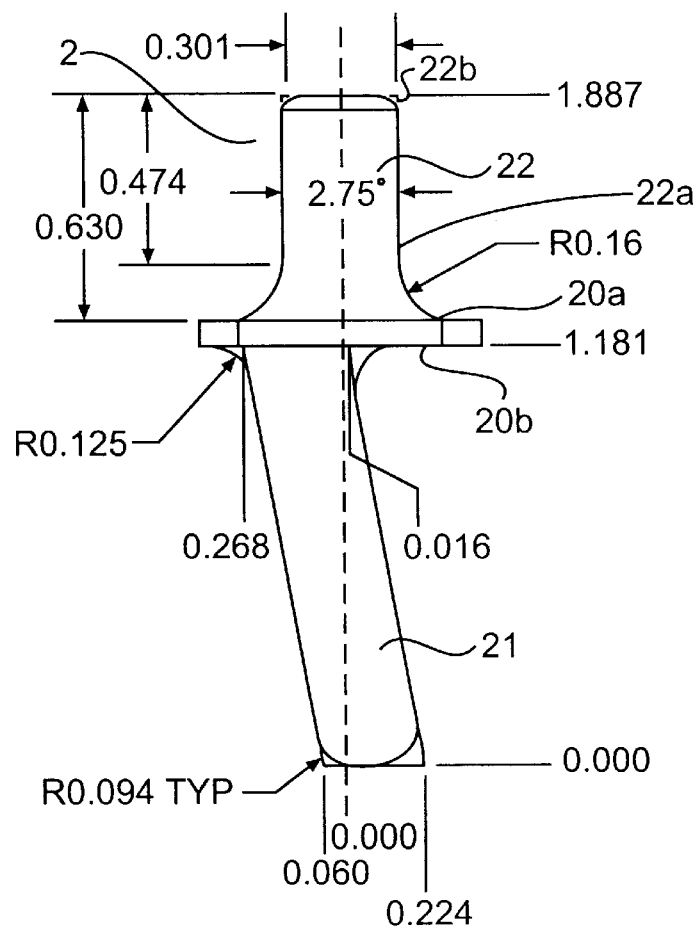
FIG. 6 is a front or cranial view of the radial component depicted in FIG. 5.
Figure 7:
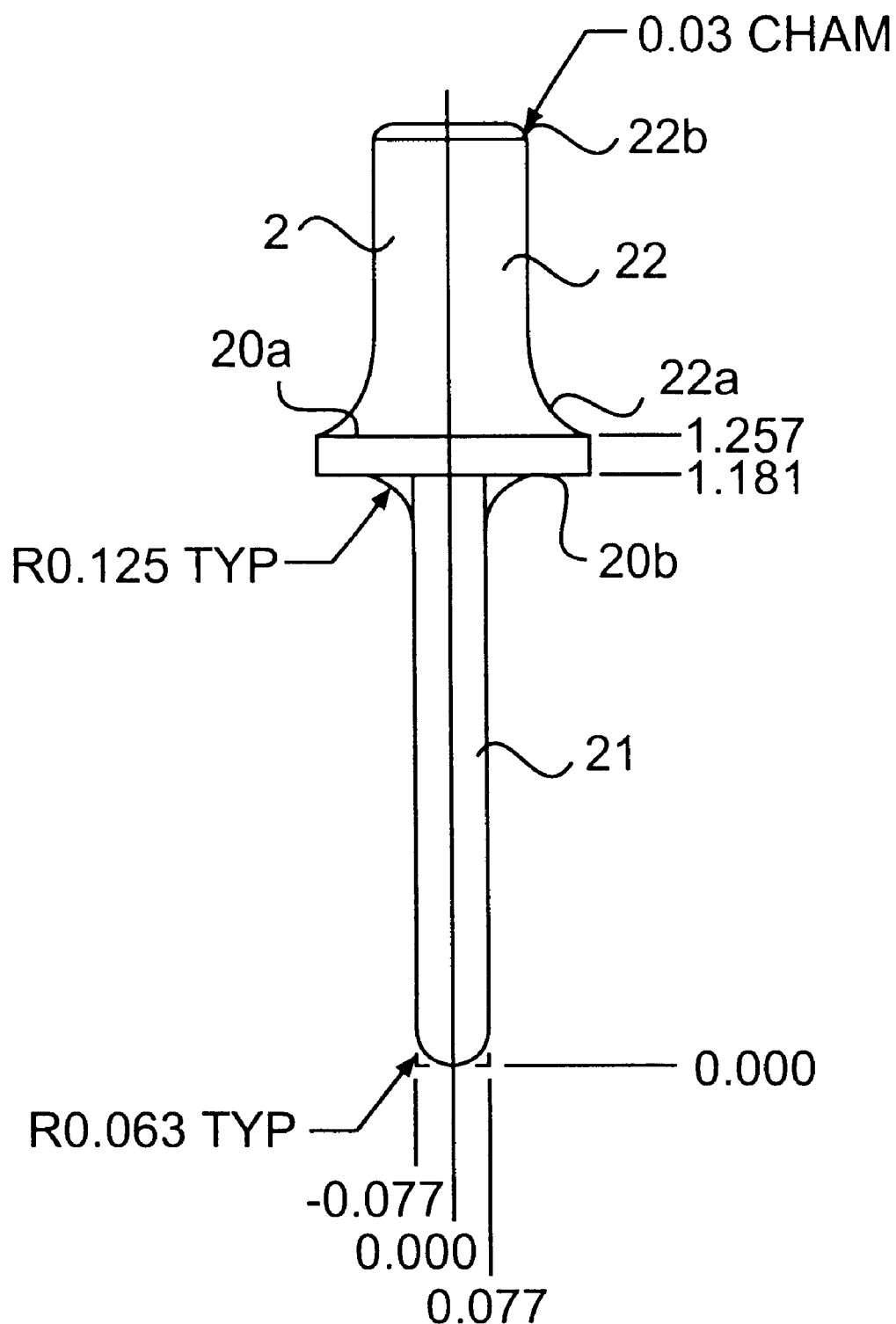
FIG. 7 is a lateral view of the radial component depicted in FIG. 5.
Figure 8:
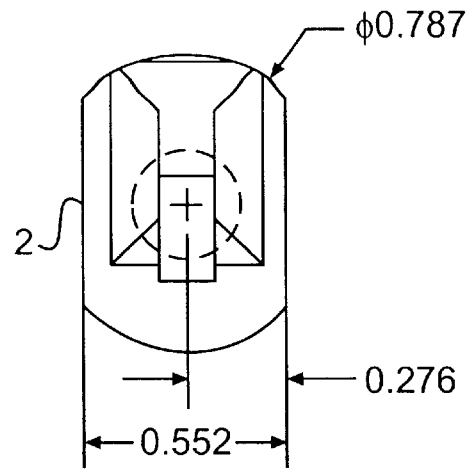
FIG. 8 is a bottom view of the radial component depicted in FIG. 5.

FIGS. 5–8 depict the radial component of a preferred embodiment of the present invention. FIG. 5 is an oblique perspective view of radial component 2. FIG. 6 is a cranial view of radial component 2. FIG. 7 is a lateral view of radial component 2. FIG. 8 is a bottom view of radial component 2.

Referring to FIGS. 5–8, radial component 2 comprises a radial stem 21, body 20 and neck 22. Radial body 20 has a proximal end or proximal face 20a and a distal end or distal face 20b. Radial neck 22 is disposed on the proximal aspect or face 20a of radial body 20 and is blended into radial body 20. Radial stem 21 is disposed on the distal face 20b of radial body 20 and is blended into radial body 20.

As discussed below, in order to implant radial component 2, the radial head is preferably removed and the stem of the radial component is implanted in the medullary canal of the radius. Radial body 20 of radial component 2 is designed to rest on the surface of the cut bone of the radius. Alternately, the abnormal bone and cartilage of both the radial head and ulna may be removed as described in U.S. patent application Ser. No. 09/207,689. In either event, body 20 does not rest on the cut bone of the ulna, nor does it interfere with the ulna. This feature allows normal motion between the radius and ulna to occur and preserves supination and pronation between the radius and ulna.

Radial body 20 is blended into radial neck 22 that angles towards the center of rotation of the original elbow joint. The neck is tapered (base 22a is wider than tip 22b); this will allow for a press fit fixation with ball component 3, which has no taper in its cylindrical hole. The dimensions of the radial component may be slightly modified for cement or porous ingrowth fixation, different sized patients, different materials, or to match the humeral component. Radial component 2 may be designed such that the stem and body are of variable sizes (small, medium, large), yet the neck size remains the same. This will allow for the system to be modular; the surgeon can pick and choose components based on patient size and ligament structure and all designs will still match since the ball component will still match/articulate with the concave surface 14a of all sizes of the humeral components. Radial component 2 is isometric.

Radial stem 21 is designed to be inserted into the medullary canal of the radius and is disposed so that it comes off of the middle of the body of the radial component at an angle that is similar or preferably identical to the radioulnar component as described in U.S. patent application Ser. No. 09/207,689. Radial stem 21 may be angled medially 74 to 84 degrees, and most preferably, is angled medially 79 degrees with respect to the sagittal midline of distal face 20b of radial body 20, so as to approximate the original angle between the original radial head and radial shaft.

As shown in the preferred embodiment depicted in FIGS. 5–8, viewed from the side, radial stem 21 preferably comes off the middle of distal face 20b of body 20, and is disposed at an angle that matches or approximates the relationship between the original radial head and radial shaft. Specifically, when viewed in a craniocaudal direction, radial stem 21 is preferably angled medially with respect to the sagittal midline of distal face 20b of radial body 20, forming an angle of approximately 79 degrees between the longitudinal axis of radial stem portion 21 and distal face 20b. Thus, with respect to the sagittal midline of radial body 20, the distal end of radial stem 21 is more medial than its proximal end (i.e., its point of attachment to distal face 20b of body 20), and the proximal end of radial stem 21 is more lateral than the distal end of radial stem 21. In this position, the longitudinal axis of radial stem 21 is also angled about 11 degrees with respect to both the longitudinal axis of radial neck 22 and a line drawn perpendicular to distal face 20b.

As will be clear to those of skill in the art, the radial component is isometric, and can be flipped over as needed to orient it for use in either the right or left elbow. Preferably, radial stem 21 has a rectangular cross-section with rounded edges and is also rounded at its distal extremity. The stem is preferably cemented in place to help stabilize the component.

Ball Component

Figure 9:
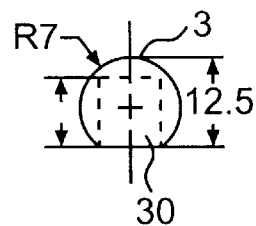
FIG. 9 is a front or cranial view of a preferred embodiment of the ball component of the present invention.
Figure 10:
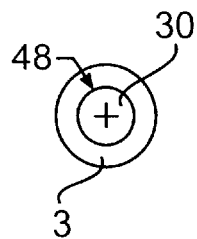
FIG. 10 is a bottom view of the ball component depicted in FIG. 9.
Figure 11A:
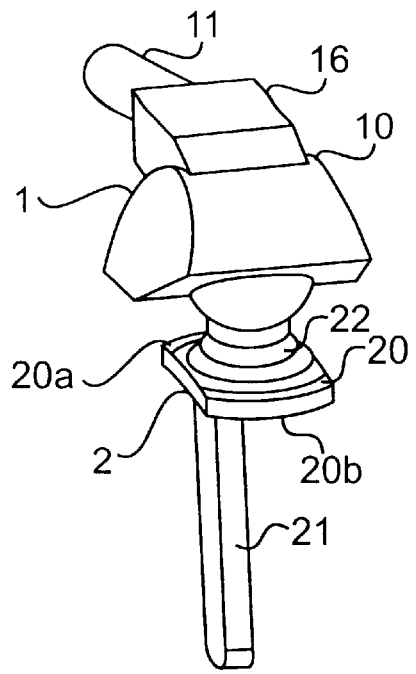
FIG. 11 a–d are perspective views of the humeral, radial and ball components in articulating engagement with each other.
Figure 11B:
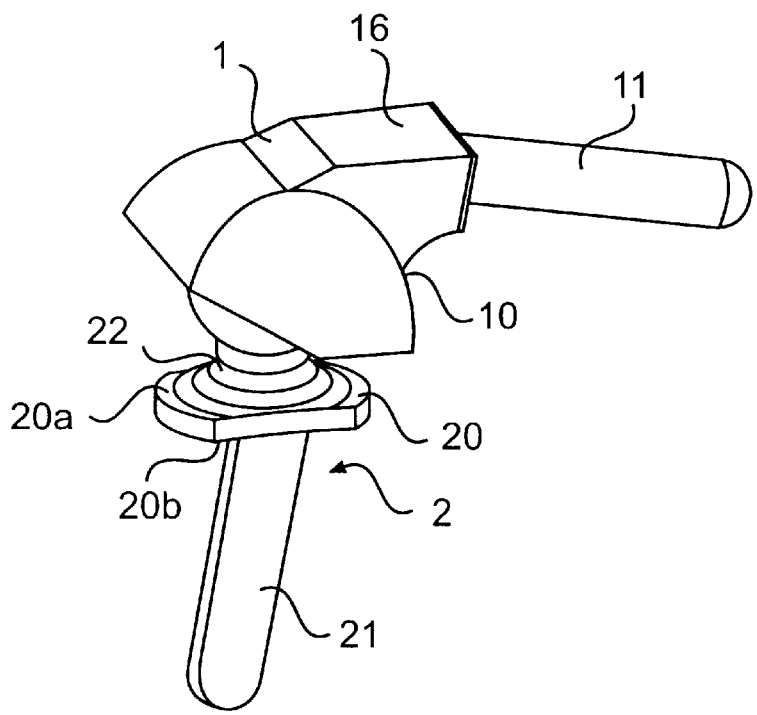
Figure 11C:
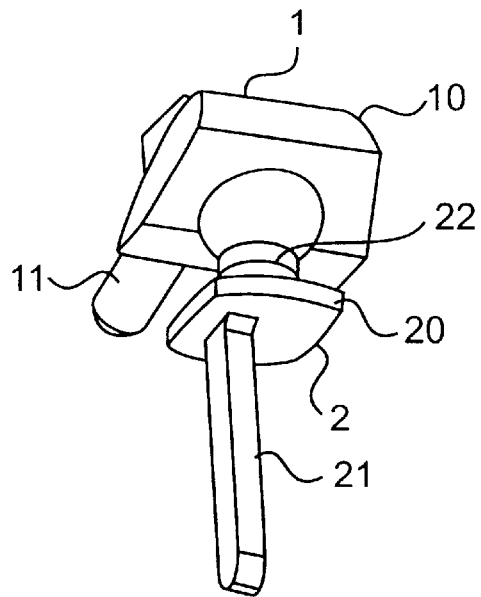
Figure 11D:
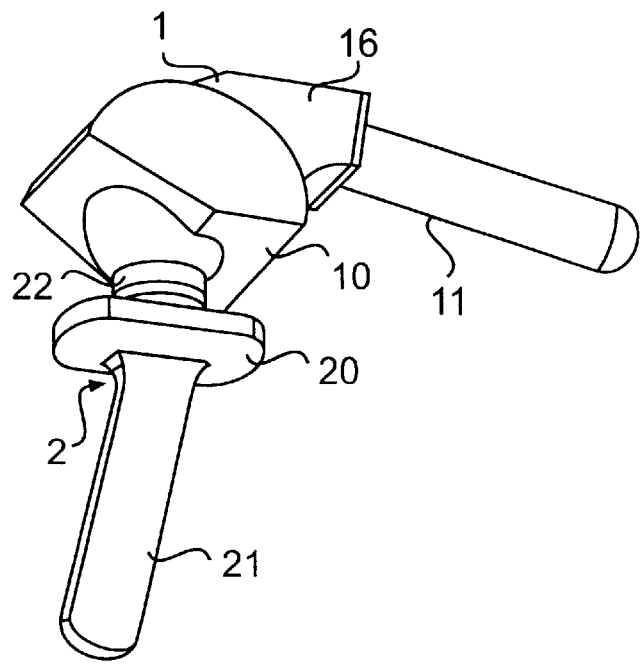

Ball component 3 is designed to be mounted on the neck of the radius. A ball component according to a preferred embodiment of the present invention is depicted in FIGS. 9–10. FIG. 9 is a cranial view of ball component 3. FIG. 10 is a bottom view of ball component 3.

Referring to FIGS. 9–10, ball component 3 is spherical on the outside and has a radius of curvature that matches the inside dimensions or radius of curvature of articulating surface 14 of humeral component 1. Ball component 3 has a hole or cavity 30 which is preferably cylindrical with no taper. Hole 30 is designed to mate with neck 22 of radial component 2. For example, in one preferred embodiment, the cylindrical hole matches the radius of the neck of the radial component about 1 centimeter from the tip of the neck. As a result, when radial neck 22 is inserted, ball component 3 is stabilized by a press fit mechanism. The cylindrical hole in the ball may have different diameters. Thus, a ball with a cylinder of increased width will sit deeper on the neck of the radial component. Likewise, one with a narrower width will not sit as deep. This allows the surgeon to try different combinations and choose the ball and radial component combination that applies the appropriate amount of tension on the ligaments about the elbow joint. The ball may be made from any suitable material, including, but not limited to, metal or ceramic. The ball component may be modified in a similar manner as the other components.

FIGS. 11a–d depict the humeral, radial and ball components according to a preferred embodiment in engagement with each other. However, variations of the preferred design may be used without departing from the spirit and scope of the invention. For example, although ball component 3 is preferably spherical, it may alternately be formed so that only the portion that actually articulates with spherically concave surface 14a of the humeral component (i.e., the spherical articular surface of ball component 3) is spherical.

In addition, although in a preferred embodiment the radial component has a neck portion for engagement with a cavity in the ball component, other configurations are possible. For example, the radial component may have an engagement portion comprising a cavity designed to mate with a neck portion disposed on the ball component. Alternately, the ball and radial component may be manufactured as a single integral piece, with or without a visible neck or delineation between them.

In a preferred embodiment, radial component 2 is machined from stainless steel 316L, Grade 5 titanium, or molded from a cobalt-chromium alloy. The radial component may be altered for composite stabilization by surface treatment of the component where it is in direct contact with bone. Humeral component 1 may be made of any suitable material, but is preferably made of medical grade crosslinked or non-crosslinked ultra-high molecular weight polyethylene ("UHMWPE"). Other suitable materials for the components may be used, including titanium, cobalt-chromium or ceramic. Ball component 3 is preferably made of metal or ceramic. Implants may be either hand machined and polished, or molded.

In the preferred embodiment, the implant system allows for approximately 127 degrees of flexion-extension, 90 degrees of mediolateral rotation and unlimited pronation and supination.

Dogs with elbow OA generally weigh between 60–90 lbs. However, the implants may be manufactured in various sizes, such as small, medium or large, allowing use of the invention in dogs with a range of body weights, such as approximately 40–120 lbs. As discussed, preferably the articular portions and engagement portions of the components are designed so that the different sizes are compatible with each other.

Humeral Cutting Guide

As discussed in more detail in the Examples which follow, implantation of the joint of the present invention is facilitated using the humeral cutting guide described herein and also in U.S. patent application Ser. No. 09/207,689, incorporated herein by reference. Preferred embodiments of the guide are depicted in FIGS. 12–15.

Figure 12:
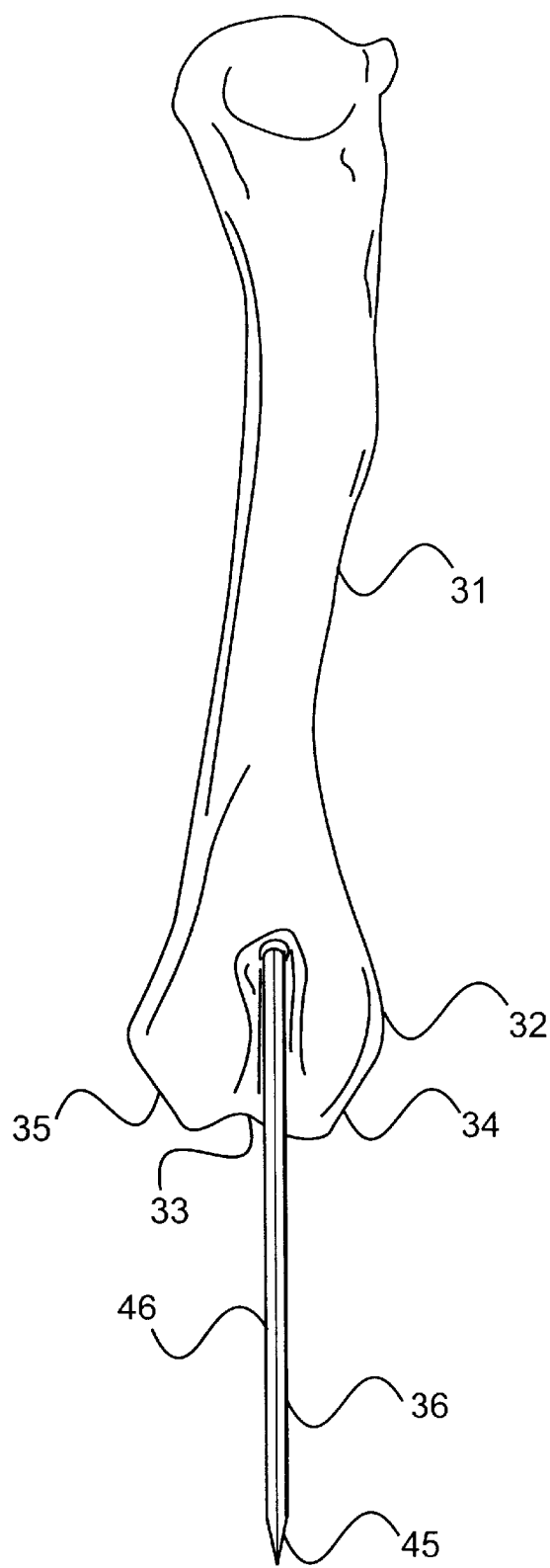
FIG. 12 is a caudal view of a left canine humerus with an intramedullary nail.

FIGS. 12–15 depict the humeral cutting guide of the present invention and its use. FIG. 12 is a caudal view of a left canine humerus 31 with intramedullary nail 36 inserted. As depicted in FIG. 12, humerus 31 has a condyle 32 at its distal end. The trochlea 33 of humerus 31 is the articular surface of the humerus. This is a potential location of arthritic cartilage in an arthritic elbow joint, and needs to be removed in connection with installing humeral component 1 of the present invention. The medial collateral ligament attaches to the medial aspect of the humerus at point of insertion 35, and the lateral collateral ligament attaches to the lateral aspect of the humerus at point of insertion 34.

Figure 13:
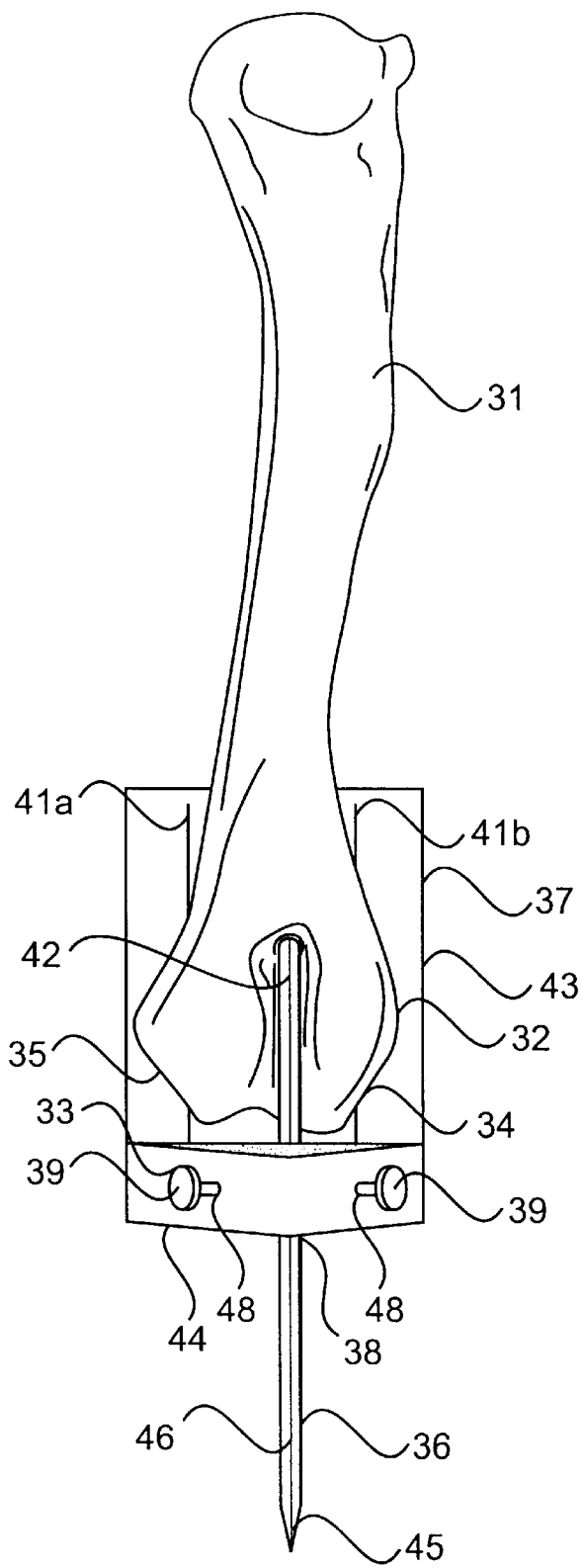
FIG. 13 is a caudal view of a canine humerus with the humeral cutting guide for use on the left elbow mounted on the intramedullary nail.
Figure 14:
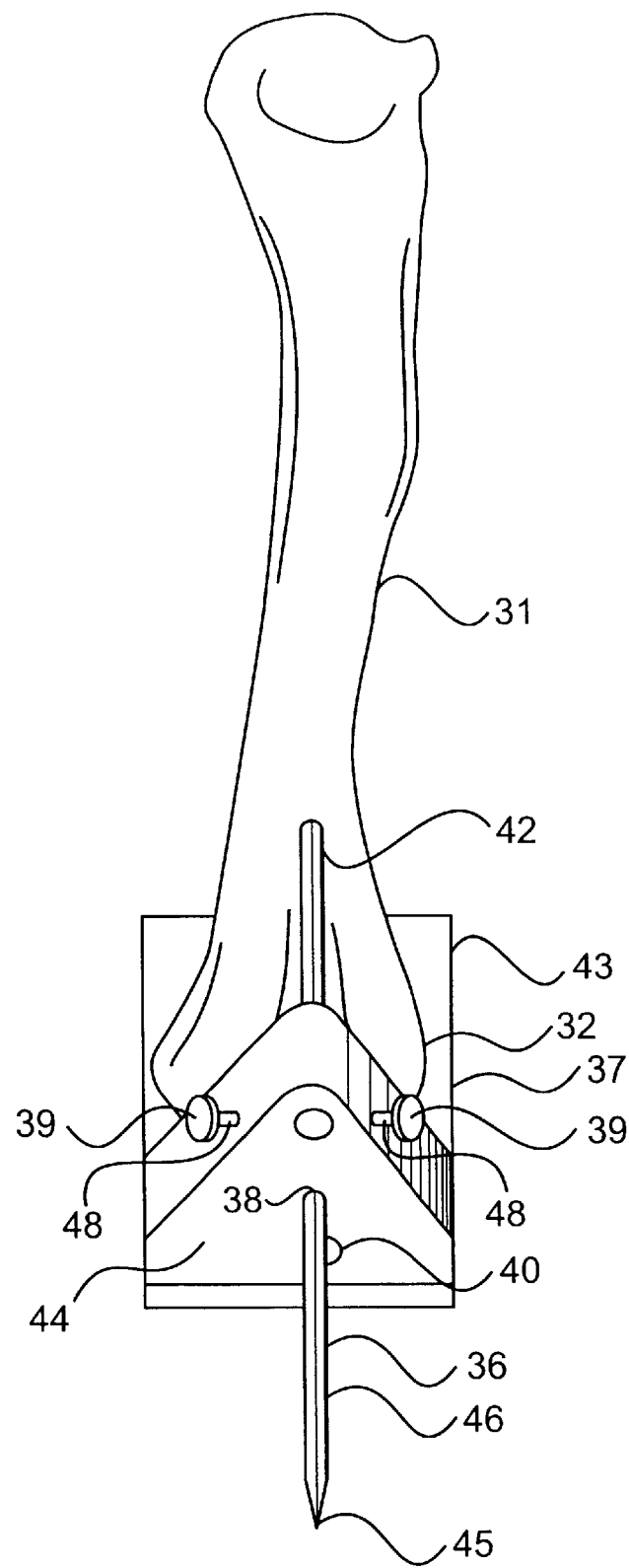
FIG. 14 is a dorsocaudal view of the humerus with the cutting guide mounted on the intramedullary nail.
Figure 15:
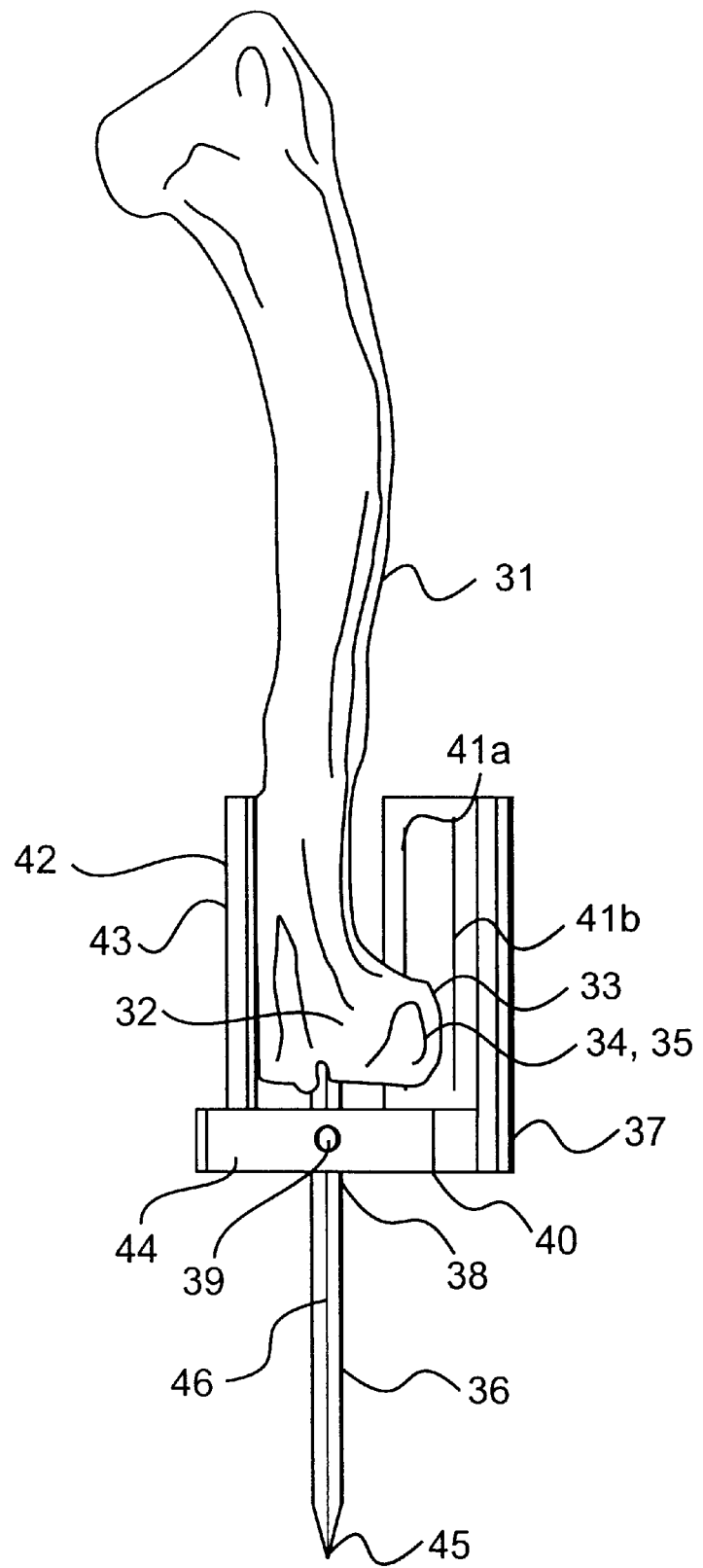
FIG. 15 is a side view of the humerus with the cutting guide mounted on the intramedullary nail.

FIG. 13 is a caudal view of humerus 31 with cutting guide 37 mounted on intramedullary nail 36. FIG. 14 is a dorso-caudal view of humerus 31 with cutting guide 37 mounted on intramedullary nail 36. FIG. 15 is a side view of humerus 31 with cutting guide 37 mounted on intramedullary nail 36.

As depicted in FIGS. 13–15, humeral cutting guide 37 has proximal or upper portion or plate 43 attached to distal or lower articular portion or plate 44. Upper or proximal portion 43 and lower or distal portion 44 are preferably planar and disposed roughly perpendicular to each other. In a preferred embodiment, lower portion 44 is wedge shaped at the end opposite the end which is attached to upper portion 43. Humeral cutting guide 37 is designed to be mounted on intramedullary nail 36 which is placed from the middle of the humeral trochlea 33 into the medullary canal of the humerus. Intramedullary nail 36 allows for mounting of cutting guide 37 on the neutral axis of the humerus. Intramedullary nail 36 preferably has a trochar tip 45 which allows for easy passage into the medullary canal. Nail 36 also preferably has flattened sides 46 to facilitate immobilization and prevent undue rotation when screws 39 in cutting guide 37 are tightened.

Referring again to FIGS. 13–15, humeral cutting guide 37 has intramedullary nail pilot hole 38 through lower portion 44. Intramedullary nail 36 is placed through nail pilot hole 38 in order to mount cutting guide 37 onto the humerus 31. To further secure cutting guide 37, screws 39 are disposed on lower portion 44 of cutting guide 37 through screw holes 48. Screws 39 are tightened into nail 36 to prevent rotation of cutting guide 37. Cutting guide 37 further has a pin pilot hole 40 in lower portion 44, through which pin 50 may be drilled to further prevent rotation of cutting guide 37.

Cutting guide slots 41a and 41b are disposed on upper portion 43 of cutting guide 37, and are located medial to the points of insertion 34 and 35 of the collateral ligaments of the humerus. Cutting guide slots 41a and 41b are parallel to each other and to cutting guide bar 42, which is disposed on the lower portion of cutting guide 37 to guide the saw used to prepare the humerus for the implants.

A saw, such as a reciprocating saw, is placed through cutting guide slots 41a and 41b to the level of cutting guide bar 42. The tip of the saw rests on bar 42 as cuts are made. This places the saw in the appropriate angle so that all articular cartilage on the trochlea of the humerus can be removed. Cutting slots 41a and 41b are located medial to the insertion points 34 and 35 of the collateral ligaments and the saw cuts are made away from the ligaments, which helps to ensure natural ligament stability of the joint after surgery. Specifically, cuts are made in the humerus using the two slots 41a and 41b of the guide. The amount of bone removed and the angles created in the condyle match the angles on sides 13a and 13b of humeral component 1.

When installed, the sides of humeral component 1 will nearly approximate the cut edge of the humeral condyle. Any discrepancy may be filled in with bone cement. Sides 13a and 13b of humeral component 1 are just below the level of the remaining condyle, allowing for full range of motion without impingement on bone. Radial component 2 rests on the cut surface of the radius. The articulation surface of the component is similar to the natural, original curvature of the intact radius.

As will be clear to those of skill in the art, the present invention can be modified for use in humans and other species. The cutting guide for the humerus depicted in FIGS. 12–15 is isometric and may be used to prepare the left or right elbow. The cutting guide may be made from any suitable material, such as stainless steel. In the preferred embodiment, it is made from 316 L stainless steel. The steel is preferably hand machined and polished to form the cutting guides and then heat treated for hardening.

The design of the present invention provides a number of advantages over other designs, including:

1. The design allows for a modular, more versatile system. The surgeon can mix and match component sizes intra-operatively for each case.

For example, a small humeral component may be used with a large radial component. This could be beneficial in a situation in which a surgeon removed too much bone from the radius and ulna. If a small radial component is used in the joint, the ligaments around the joint would be loose. The problem may be corrected by simply using a larger radial component because its body has a thicker base. Because the invention is modular, the humeral component does not have to be increased. This avoids potential problems which could result from the increased width of the larger humeral component.

2. The design allows for motion between the radius and ulna (preserves supination and pronation of the antebrachium).

3. The surgical technique for implantation of the components is simpler.

4. The manufacturing of the components is less expensive.
5. A caudal approach (via proximal ulnar ostectomy) can be performed to implant the components. This approach improves surgical view of the joint, makes surgical implantation easier, preserves both medial and lateral humeral-radial collateral ligaments, and reduces postoperative patient morbidity. A lateral approach may also be used to implant these components if the surgeon prefers.

Surgical approaches used to implant other designs may involve avulsion of the lateral collateral ligament and medial luxation of the joint. Such approaches may increase postoperative morbidity by increasing postoperative pain and periarticular fibrosis.

6. Since the ball and socket have nearly 100% contact with each other at the articular surface, mechanical load will be evenly distributed. Even distribution of load, given a larger area of contact surface, will decrease stress and thus reduce wear of the components. Existing elbow designs have an increased potential for uneven loading and increased wear if the implants are not positioned properly.
7. The implant is nonconstrained. This is an important feature which addresses not only the articular surfaces but the motion allowed between components. Unconstrained systems, e.g., most total knee and hip systems, allow motion in more than one plane between components. This makes the ligaments and other periarticular tissues share in much of the mechanical load when the limb is used. The more constrained a system is the more load at the bone-cement and implant-cement interfaces. Increased load bearing can lead to a shorter time of failure at the implant-bone, implant-cement, or cement-bone interface. Many human elbow systems are constrained or semiconstrained. The design of the present invention will allow for flexion-extension, mediolateral rotation, and supination-pronation.

Nonconstrained systems have no mechanical linkage between the implants and rely on the natural ligaments of the body for stability. An advantage of the design of the present invention is reduced wear between the components and reduced stress at the component-cement and cement-bone interfaces. This increases life span of the implants. The articulating surfaces of the components allow smooth articulation and greater range of motion in flexion and extension than in even the normal joint. This eliminates the likelihood of binding during use.

8. All three components are isometric—they can be used in left or right limbs. This reduces inventory and manufacturing costs.
9. No osteotomies need to be surgically repaired to implant the components. Cartilage and its associated bone are removed so the components can be implanted. However, osteotomies requiring surgical repair are not needed to get the necessary exposure to put in the components. This decreases costs, surgical time, and patient morbidity.
10. Prognosis is improved and morbidity associated with surgery and the implant is reduced.
11. The implant design incorporates a combination of bone cement and porous ingrowth technologies. The surfaces of the stems on the components can be easily altered for porous ingrowth fixation.

The grooves on the sides of the humeral component increase the surface area for increased fixation between the cement and the component. The sizes and shapes of grooves and stems allow for increased cement mantle size without decreasing the strength of the components.

12. The humeral cutting guide ensures that the appropriate amount of bone is removed for each component. This decreases the likelihood of removal of too much bone stock.
13. Removal of the articular cartilage of the ulna is left to the discretion of the surgeon. If the ulna is left intact, it will reduce the likelihood of ulna fracture, periarticular fibrous tissue formation and heterotopic bone formation.
14. The body portion of the radial component is designed to rest on the surface of the cut bone of the radius. No fixation or connection of the component to the ulna is required. No ulnar component is needed. Articulation is provided by the simple, isometric ball and socket joint of the invention, implanted as described in the medullary canals of the radius and humerus.

Short-term results (2 months) with the implants of the present invention show that following surgery the dogs have functional use of the surgery leg with no unexpected complications.

Accordingly, one embodiment of the invention is directed to an elbow endoprosthesis for replacing an elbow in a patient comprising a humeral component, a radial component and a ball component. The humeral component has a condylar portion and a stem portion. The condylar portion is adapted to be received in a resected portion of a distal humerus between the medial and lateral aspects of the humeral condyles. The condylar portion has a proximal end and a distal end. A proximal portion is disposed at the proximal end; an isometric articulating surface comprising a concave socket, a first side and a second side opposite said first side are disposed at the distal end. The proximal portion has a longitudinal axis and a first cross-sectional area. The articulating surface comprises a concave socket disposed on the craniodistal aspect of the distal end of the condylar portion, midway between the first side and the second side. The humeral stem portion is attached to the proximal end of the proximal portion of the condylar portion. The stem portion is adapted to be received in the medullary canal of the distal humeral shaft. The humeral stem portion has a proximal end and a longitudinal axis which is angled cranially with respect to the longitudinal axis of the proximal portion of the condylar portion so that the condylar portion and stem portion approximate the original angle between the humeral condyle and the humeral shaft. In addition, the stem portion has a second cross-sectional area which is smaller than the first cross-sectional area of the proximal portion, thereby forming a shoulder between the humeral stem portion and the proximal portion. Optionally, a depression adapted to receive the anconeal process of the ulna may be disposed on the caudal aspect of the distal end of the condylar portion. This allows the ulna to move normally during flexion and extension of the joint.

The radial component comprises a body portion having a proximal face and a distal face, an engagement portion attached to the proximal face, and a radial stem portion attached to the distal face. The stem is adapted to be received in the medullary canal of a proximal radial shaft.

The ball component is adapted to be mounted on the radial engagement portion and comprises a spherical articular surface for articulation with the concave socket of the humeral component. As used herein, the term "spherical articular surface" refers to the portion of the ball component that actually articulates with the concave socket of the humeral component. The radial engagement portion preferably comprises a radial neck portion and the ball component preferably has a hole or cavity therein adapted to receive the radial neck portion of the radial component. In a preferred embodiment, the radial and ball components are manufactured as two separate pieces, and the ball is mounted on the radial component in connection with implanting the endoprosthesis. Alternately, the radial and ball components may be permanently affixed to one another or manufactured as a single integral piece. In still another embodiment, a neck portion may be disposed on the ball component and the radial engagement portion may comprise a cavity for receiving the neck portion on the ball component.

In a preferred embodiment, the humeral stem portion has a rounded proximal end and its longitudinal axis is angled cranially about 5 degrees with respect to the longitudinal axis of the proximal portion. The humeral stem portion may have one or more grooves to facilitate affixing it in place with cement. Preferably, these grooves run longitudinally along the stem and have a reverse wedge profile.

The radial stem portion may be rounded at its distal end. The radial stem portion is preferably angled medially with respect to the radial body portion, forming an angle of about 79 degrees between the radial stem portion and the distal face of the radial component, such that the proximal end (the point of attachment of the radial stem portion to the radial body portion) is disposed lateral to the distal end of the radial stem. Preferably, all three components are isometric.

Another embodiment of the invention is directed to an elbow endoprosthesis for replacing an elbow, such as a canine elbow, comprising a ball and socket joint. Preferably, the ball and socket joint comprises a humeral component, a radial component and a ball component. The humeral component has a proximal end and a distal end, an articulating surface disposed at the distal end, the articulating surface comprising a concave socket, and humeral mounting means disposed at the proximal end for mounting the humeral component on the distal humeral shaft. The radial component comprises a radial body portion having a proximal end and a distal end, radial mounting means disposed at the distal end of the radial body portion for mounting the radial component on the proximal radial shaft, and a radial engagement portion attached to the proximal end of the radial body portion. The ball component comprises a spherical articular surface for articulation with the concave socket. The ball component is adapted to be mounted on or otherwise affixed to the radial engagement portion.

The present invention is also directed to methods for implanting an elbow endoprosthesis in an elbow joint, such as a canine elbow joint. One such method comprises the steps of removing the trochlea of the humerus, removing the articular surface of the radius (i.e., the radial head) and cancellous bone from the proximal medullary canal of the radius, and, in any order, implanting a humeral component into the medullary canal of the humerus, and implanting a radial component into the medullary canal of the radius. Optionally, the method may further comprise the step of removing the articular surface of the ulna.

Preferably, the radial component is adapted to receive a ball component thereon. The humeral component has a concave socket articulating surface for articulating with the ball component. The ball component may be mounted on the radial component before or after the radial component is implanted into the medullary canal of the radius. The method may further comprise the steps of sequentially mounting one or more ball components of different sizes on the radial component and allowing articulation between the humeral component and the combined radial and ball components to determine the ball component which has the best fit. The surgeon can select the ball component providing the appropriate amount of tension on the structures surrounding the joint. Alternately, the ball component and radial component may be formed as a single integral piece.

The humeral and radial components may be affixed in place using any suitable material or bone cement, such as PMMA or a bioactive cement.

The trochlea of the humerus is preferably removed using the humeral cutting guide described herein. The articular surface of the radius is preferably removed by using an oscillating saw to remove the radial head.

Specifically, the trochlea of the humerus is preferably removed using a humeral cutting guide, the humeral cutting guide comprising a proximal portion, the proximal portion having two parallel cutting slots therethrough, a distal portion having a first face, the proximal portion being affixed to the first face such that the proximal portion and distal portion are substantially perpendicular to each other, and a guide bar, the guide bar being disposed on the first face of the distal portion perpendicular to the first face and parallel to the proximal portion.

In this method, the step of removing the trochlea may comprise the steps of drilling a first hole approximately 10 cm from the trochlear notch of the humerus proximally up the medullary canal, placing a first pin in the first hole until it engages cortical bone, mounting the cutting guide on the first pin, and removing the trochlea of the humerus. The step of removing the articular surface of the radius and cancellous bone of the radius may comprise the steps of removing the radial head and removing cancellous bone to a depth of about 1 cm from the medullary canal of the radius.

In a preferred embodiment of the method, the humeral component is installed first. In order to fix the components, a cement, such as PMMA, may be placed into the medullary canal of the humerus and radius. The respective stem of each component is then inserted and is held in place until the cement hardens.

Another embodiment of the invention is directed to a method of replacing a quadruped's elbow comprising removing the trochlea of the humerus and the articular surface of the radius of the quadruped's elbow joint, and affixing a ball and socket endoprosthetic joint in place of the removed humeral trochlea and articular surface of the radius. Optionally, the articular surface of the ulna may also be removed. Preferably, the quadruped is a canine.

The following experiments are offered to illustrate embodiments of the invention and should not be viewed as limiting the scope of the invention.

Example 1

Implantation of Endoprosthetic Joint

Each dog was placed in lateral recumbency and a standard aseptic preparation of the forelimb was performed.

A 10-cm skin incision was made extending from the caudal, distal aspect of the humerus to the caudal, mid-ulna. Sharp dissection was used to expose the proximal third of the ulna. An ulnar osteotomy was performed 3 cm below the level of the radial head. The humeral-ulnar and radial-ulnar ligaments were transected and the ulna was luxated proximally. This provided excellent exposure of the distal humerus and proximal radius while preserving the medial and lateral humeral-radial collateral ligaments.

The humerus was prepared for implantation of the humeral component as described in U.S. patent application Ser. No. 09/207,689. More specifically, referring to FIGS. 12–15 the humerus was prepared for implantation of the humeral component using the specially designed humeral cutting guide 37 of the present invention. A drill bit (5 to 9 mm) was used to drill a first hole into the humeral medullary canal approximately 5 cm, from distal to proximal, starting at the middle and dorsal aspect of the trochlear notch. The drill hole ran approximately 10 cm from the dorsal aspect of the trochlear notch of the humerus proximally up the medullary canal. The identical drill bit was used to drill a hole perpendicular to the long axis of the humeral shaft into the trochlear notch. A ¼" pin or intramedullary nail 36 was placed in the first hole in the humeral medullary canal, following the direction of the drill hole, and was advanced up the shaft of the humerus, until it engaged cortical bone. Humeral cutting guide 37 was mounted onto the humerus by sliding guide 37 onto nail 36. Cutting guide slots 41a and 41b were then aligned evenly on either side of the condyle 32 to match the medial and lateral extremes of the cranial aspect of the humeral articular cartilage, and guide 37 was temporarily nailed into place. Humeral cutting guide 37 was secured in place by drilling a pin through pilot hole 40 in cutting guide 37 and into the humeral condyle. This prevented rotation of the cutting guide. Screws 39 in cutting guide 37 were tightened to further secure cutting guide 37.

The trochlea/articular cartilage of the humeral condyle was removed by using a saw such as a power driven saw (e.g., minidriver; 3M) through cutting guide slots 41a and 41b. The bone cut was made with the saw blade placed through the cutting slots 41a and 41b located on cutting guide 37. Cutting guide 37 was then removed. The cut ends were made smooth using a flat bone file. Care was taken not to remove more bone stock than necessary. The humerus was flushed and suctioned.

An ostectomy of the radial head was performed using an oscillating saw. The medullary canal of the radius was prepared for implantation of the radial component as described in U.S. patent application Ser. No 09/207,689. More specifically, the radial shaft was prepared for the component by drilling the shaft with a drill bit to a depth of approximately 4 cm. The cancellous bone was removed (to a depth of about 1 cm) from the radius. The bone was flushed. If indicated, arthritic bone of the ulna may be removed at this stage. Optionally, the anconeal process of the ulna may be left intact. In this situation, a humeral component with a caudal depression is used.

The humeral component was positioned within the humerus. Stem 11 of the component should slide freely into the humeral canal. Humeral component 1 was manually positioned and aligned so that shoulder 9 of the implant rested against the distal aspect of the humeral shaft. The curved, polished articular surface of the component followed the curvature of and protruded just distal to the cut bone of the humeral condyle. PMMA was prepared and placed into the humeral medullary canal and adjacent to the cut surface of the humerus. The humeral component was implanted.

The radial component was positioned within the radius. The radial component was fixed in place by placing cement in the medullary canal, positioning the radial component, and allowing the cement to harden. A trial ball component was placed on the neck of the radial component and the joint was reduced. The joint was placed through a range of motion and the surgeon determined if the functional length of the radial component needed to lengthened or shortened based on the tension of the tissues about the elbow. After the appropriate ball component cylinder diameter was determined, the ball component was positioned on the neck of the radial component and the joint was reduced. The ulnar osteotomy site was reduced and stabilized. The soft tissues were closed in a routine fashion.

In addition to the stems of the humeral and radial components described herein, any suitable mounting means may be used to mount the radial and humeral components onto their respective bones. Further, although the humeral and radial components of the preferred embodiment were secured using bone cement, in an alternate embodiment the components may be further secured using screws. For example, a 2.7 mm diameter screw (approximately 16–20 mm in length) may be positioned from a preplaced glide hole in the lateral aspect of the condyle into the humeral implant and again from the medial side. This causes compression between the lateral and medial aspects of the humeral condyle and the implant.

Example 2

Post-Operative Results

The ball and socket design was successfully implanted in two dogs using the procedures of Example 1. The surgical procedures went smoothly and surgical time was under two hours for each dog. Within two weeks of surgery, both dogs used the operated leg during walking. At eight weeks after surgery, the dogs used the leg during each step during walking and at a trot. The use of the limb was approximately 75% of normal use. Range of motion at 8 weeks was 75 degrees.

Other embodiments and uses of the invention will be apparent to those skilled in the art from consideration of the specification and practice of the invention disclosed herein. All documents and references referred to herein, including all U.S. and foreign patents and patent applications (including, but not limited to, U.S. patent application Ser. No. 09/207,689 and U.S. Provisional Patent Application Serial No. 60/137,514) are specifically and entirely hereby incorporated herein by reference. Although the invention has been described in connection with the canine elbow, it can be easily adapted for use in other species, including other quadrupeds and man. The specification should be considered exemplary only with the true scope and spirit of the invention indicated by the following claims. As will be easily understood by those of ordinary skill in the art, variations and modifications of each of the disclosed embodiments can be easily made within the scope of this invention as defined by the following claims.

I claim:

1. An elbow endoprosthesis comprising:
    a humeral component, the humeral component comprising:
        (i) a condylar portion adapted to be received in a resected portion of a distal humerus between the medial and lateral aspects of the humeral condyles, the condylar portion having a proximal end and a distal end, an isometric articulating surface disposed at the distal end, the articulating surface comprising a concave socket; and
        (ii) a humeral stem portion attached to the proximal end of the condylar portion, the humeral stem adapted to be received in the medullary canal of the distal humeral shaft, the humeral stem portion angled cranially with respect to the condylar portion to approximate the original angle between the humeral condyle and the humeral shaft;
    a radial component, the radial component comprising:
        (i) a radial body portion having a proximal face and a distal face;
        (ii) a radial stem portion attached to the distal face of the radial body portion adapted to be received in the medullary canal of a proximal radial shaft; and (iii) a radial engagement portion attached to the proximal face of the radial body portion; and a ball component, the ball component comprising a spherical articular surface for articulation with the concave socket, said ball component adapted to be mounted on the radial engagement portion.

2. The endoprosthesis of claim 1 wherein the radial engagement portion comprises a radial neck portion.

3. The endoprosthesis of claim 2 wherein said ball component has a cavity therein adapted to receive the radial neck portion of the radial component.

4. The endoprosthesis of claim 1 wherein the radial component and the ball component are permanently affixed to one another.

5. The endoprosthesis of claim 1 wherein the radial component and the ball component comprise a single integral piece.

6. The endoprosthesis of claim 1 further comprising a depression disposed on a caudal aspect of the distal end of the condylar portion, said depression adapted to receive an anconeal process of an ulna.

7. The endoprosthesis of claim 1 further comprising one or more grooves in the humeral stem portion.

8. The endoprosthesis of claim 1 wherein said condylar portion further comprises a proximal portion disposed at the proximal end, the humeral stem portion being attached to said proximal portion, the proximal portion having a longitudinal axis and a first cross-sectional area, and wherein said condylar portion further comprises a first side and a second side disposed at the distal end, the concave socket being disposed on the craniodistal aspect of the distal end of the condylar portion, midway between the first side and the second side, and wherein said humeral stem portion comprises a proximal end and a longitudinal axis angled cranially with respect to the longitudinal axis of the proximal portion to approximate the original angle between the humeral condyle and the humeral shaft, the stem portion having a second cross-sectional area smaller than the first cross-sectional area of the proximal portion, thereby forming a shoulder between the humeral stem portion and the proximal portion.

9. The endoprosthesis of claim 8 wherein the longitudinal axis of the humeral stem portion is angled cranially about 5 degrees with respect to the longitudinal axis of the proximal portion.

10. The endoprosthesis of claim 1 wherein the humeral stem portion further comprises a rounded proximal end.

11. The endoprosthesis of claim 1 wherein the humeral component is isometric.

12. The endoprosthesis of claim 1 wherein the radial component is isometric.

13. The endoprosthesis of claim 1 wherein the radial stem portion is angled medially with respect to the radial body portion, forming an angle of about 79 degrees between the radial stem portion and the distal face of the radial component, such that the point of attachment of the radial stem portion to the radial body portion is disposed lateral to the distal end of the radial stem.

14. The endoprosthesis of claim 1 wherein the radial stem portion is rounded at its distal end.

15. The endoprosthesis of claim 1 wherein the elbow is a replacement for a canine elbow.

16. An elbow endoprosthesis for replacing an elbow comprising a ball and socket joint wherein said ball and socket joint comprises:

a humeral component having a proximal end and a distal end, the humeral component comprising articulating surface disposed at the distal end, the articulating surface comprising a concave socket, the humeral mounting means disposed at the proximal end for mounting the humeral component on the distal humeral shaft;

a radial component, the radial component comprising a radial body portion having a proximal end and a distal end, radial mounting means disposed at the distal end of the radial body portion for mounting the radial component on the proximal radial shaft, and a radial engagement portion attached to the proximal end of the radial body portion; and a ball component, the ball component comprising a spherical articular surface for articulation with the concave socket, said ball component adapted to be mounted on the radial engagement portion.

17. The elbow endoprosthesis of claim 16 wherein the elbow is a replacement for a canine elbow.

18. A method for implanting an elbow endoprosthesis in an elbow joint, comprising the steps of:

removing the trochlea of the humerus;

removing the articular surface of the radius and cancellous bone from the proximal medullary canal of the radius; and, in any order, implanting a humeral component into the medullary canal of the humerus; and implanting a radial component, which is adapted to receive a ball component thereon, into the medullary canal of the radius;

wherein the humeral component comprises (i) a condylar portion adapted to be received in a resected portion of a distal humerus between the medial and lateral aspects of the humeral condyle, the condylar portion having a proximal end and a distal end, an isometric articulating surface disposed at the distal end, the articulating surface comprising a concave socket, and (ii) a humeral stem portion attached to the proximal end of the condylar portion, the humeral stem adapted to be received in the medullary canal of the distal humeral shaft, the humeral stem portion angled cranially with respect to the condylar portion to approximate the original angle between the humeral condylar and the humeral shaft;

and wherein the radial component comprises:

(i) a radial body portion having a proximal face and a distal face;

(ii) a radial stem portion attached to the distal face of the radial body portion adapted to be received in the medullary canal of a proximal radial shaft; and (iii) a radial engagement portion attached to the proximal face of the radial body portion;

and wherein the ball component comprises a spherical articular surface for articulation with the concave socket, said ball component adapted to be mounted on the radial engagement portion.

19. The method of claim 18 wherein the humeral component further comprises a depression disposed on a caudal aspect of the distal end of the condylar portion, said depression adapted to receive an anconeal process of an ulna.

20. A method of replacing a quadruped's elbow comprising:

removing the humeral trochlea and the articular surface of the radius of the quadruped's elbow joint; and affixing a ball and socket endoprosthestic joint in place of the removed humeral trochlea and articular surface of the radius wherein the endoprosthetic joint comprises:

a humeral component, the humeral component comprising
(i) a condylar portion adapted to be received in a resected portion of a distal humerus between the medial and lateral aspects of the humeral condyle, the condylar portion having a proximal end and a distal end, an isometric articulating surface disposed at the distal end, the articulating surface comprising a concave socket, and
(ii) a humeral stem portion attached to the proximal end of the condylar portion, the humeral stem adapted to be received in the medullary canal of the distal humeral shaft, the humeral stem portion angled cranially with respect to the condylar portion to approximate the original angle between the humeral cordylar and the humeral shaft;

a radial component, the radial component comprising:
(i) a radial body portion having a proximal face and a distal face;
(ii) a radial stem portion attached to the distal face of the radial body portion adapted to be received in the medullary canal of a proximal radial shaft; and
(iii) a radial engagement portion attached to the proximal face of the radial body portion;

and wherein the ball component comprises a spherical articular surface for articulation with the concave socket, said ball component adapted to be mounted on the radial engagement portion.

* * * * *